United States Patent
Wang

(10) Patent No.: US 11,447,764 B2
(45) Date of Patent: Sep. 20, 2022

(54) SITE-SPECIFIC GENERATION OF PHOSPHORYLATED TYROSINES IN PROTEINS

(71) Applicant: The Regents of the University of California, Oakland, CA (US)

(72) Inventor: Lei Wang, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 77 days.

(21) Appl. No.: 16/484,757

(22) PCT Filed: Feb. 13, 2018

(86) PCT No.: PCT/US2018/018063
§ 371 (c)(1),
(2) Date: Aug. 8, 2019

(87) PCT Pub. No.: WO2018/148754
PCT Pub. Date: Aug. 16, 2018

(65) Prior Publication Data
US 2019/0359965 A1  Nov. 28, 2019

Related U.S. Application Data

(60) Provisional application No. 62/458,557, filed on Feb. 13, 2017.

(51) Int. Cl.
| | |
|---|---|
| *C12N 9/88* | (2006.01) |
| *C07F 9/12* | (2006.01) |
| *C07F 9/24* | (2006.01) |
| *C12N 9/00* | (2006.01) |
| *C12N 15/52* | (2006.01) |
| *C12N 15/63* | (2006.01) |

(52) U.S. Cl.
CPC .................. *C12N 9/88* (2013.01); *C07F 9/12* (2013.01); *C07F 9/242* (2013.01); *C12N 9/93* (2013.01); *C12N 15/52* (2013.01); *C12N 15/63* (2013.01); *C12N 2310/314* (2013.01); *C12Y 601/01026* (2013.01)

(58) Field of Classification Search
CPC . C12N 9/88; C12N 9/93; C12N 15/52; C12N 15/63; C12N 2310/314; C07F 9/12; C07F 9/242; C12Y 601/01026
See application file for complete search history.

(56) References Cited

U.S. PATENT DOCUMENTS 9,085,514 B2   7/2015 Lemke et al.

FOREIGN PATENT DOCUMENTS

| WO | WO 2001-74827 A1 * | 10/2001 |
| WO | 2015/006555 A2 | 1/2015 |

OTHER PUBLICATIONS

Whisstock et al. Quaterly Reviews of Biophysics, 2003, "Prediction of protein function from protein sequence and structure", 36(3):307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Kisselev L., Polypeptide release factors in prokaryotes and eukaryotes: same function, different structure. Structure, 2002, vol. 10:8-9.*
Arslan, T., et al., "Structurally modified firefly luciferase." Effects of amino acid substitution at position 286, Journal of the American Chemical Society, 1997, vol. 119, No. 45, pp. 10877-10887. See abstract; pp. 10878-10880,10886; and schemes 3, 4.
Chao, H.-G. et al., "Synthesis and application of Fmoc-G-[bis 20-22,26,27 (dimethylamino) phosphono] tyrosine, a versatile protected phosphotyrosine equivalent," The Journal of Organic Chemistry, 1995, vol. 60, pp. 7710-7711. See p. 7710; scheme 1; and tables 1,2.
Rothman, D. M. et al., "Caged phosphoproteins" Journal of the American Chemical Society, 2005, vol. 127, No. 3. pp. 846-847 See p. 846: and scheme 2.
Humphrey. D. eta!., "In situ photoactivation of a caged phosphotyrosine peptide derived from focal adhesion kinase temporarily halts lamellar extension of single migrating tumor cells", Journal of Biological Chemistry, 2005, vol. 280, No. 23, pp. 22091-22101 See abstract: p. 22095: and figure 1.

(Continued)

*Primary Examiner* — Iqbal H Chowdhury

(57) ABSTRACT

Provided herein are novel materials and methods for site-specific incorporation of phosphotyrosines into proteins. The novel methods of the invention encompass the use of a novel aminoacyl tRNA synthetase capable of charging compatible tRNAs with a phosphotyrosine precursor. The phosphotyrosine precursor is then incorporated, site-specifically, into a protein at sites where phosphotyrosine residues are desired. The phosphotyrosine precursors are subsequently treated to convert them into phosphotyrosine residues, yielding proteins with phosphotyrosines at selected sites. The scope of the invention encompasses novel aminoacyl tRNA synthetases, novel phosphotyrosine precursors, and methods of using these materials to create site-specific phosphorylated tyrosine residues in a protein.

5 Claims, 4 Drawing Sheets

Specification includes a Sequence Listing.

(56) References Cited

OTHER PUBLICATIONS

Chen, S. et al .. "Incorporation of Phosphorylated Tyrosine into Proteins: In Vitro Translation and Study of Phosphorylated I KB-u and Its Interaction with NF-KB" Journal of the American Chemical Society, 2017, vol. 139, pp. 14098-14108. [Epub.]Sep. 12, 2017 See abstract: pp. 14099-14100. 14104-14106: and figure 1.

Lacey et al., 2015, Expanding the Library and Substrate Diversity of the Pyrrolysyl-tRNA Synthetase to Incorporate Unnatural Amino Acids Containing Conjugated Rings Chembiochem 14: 2100-2105.

Hoppmann et al., 2014 Genetically Encoding Photoswitchable Click Amino Acids in *Escherichia coli* and Mammalian Cells. Angew. Chem. Int. Ed. Engl. 53, 3932-3936.

\* cited by examiner

SEQUENCE LISTING

```
<160> NUMBER OF SEQ ID NOS: 3

<210> SEQ ID NO 1
<211> LENGTH: 1365
<212> TYPE: DNA
<213> ORGANISM: Methanosarcina mazei
<220> FEATURE:
<223> OTHER INFORMATION: mutant pyrrolysyl-tRNA synthetase

<400> SEQUENCE: 1
atggataaaa agcctctgaa cactctgatt tctgcgaccg gtctgtggat gtcccgcacc      60
ggcaccatcc acaaaatcaa acaccatgaa gttagccgtt ccaaaatcta cattgaaatg     120
gcttgcggcg atcacctggt tgtcaacaac tcccgttctt ctcgtaccgc tcgcgcactg     180
cgccaccaca aatatcgcaa aacctgcaaa cgttgccgtg ttagcgatga agatctgaac     240
aaattcctga ccaaagctaa cgaggatcag acctccgtaa aagtgaaggt agtaagcgct     300
ccgacccgta ctaaaaaggc tatgccaaaa agcgtggccc gtgccccgaa acctctggaa     360
aacaccgagg cggctcaggc tcaaccatcc ggttctaaat tttctccggc gatcccagtg     420
tccacccaag aatctgtttc cgtaccagca agcgtgtcta ccagcattag cagcatttct     480
accggtgcta ccgcttctgc gctggtaaaa ggtaacacta cccgattac tagcatgtct     540 gcaccggtac aggcaagcgc cccagctctg actaaatccc agacggaccg tctggaggtg     600
ctgctgaacc caaaggatga atctctctg aacagcggca agcctttccg tgagctggaa     660
agcgagctgc tgtctcgtcg taaaaaggat ctgcaacaga tctacgctga ggaacgcgag     720
aactatctgg gtaagctgga gcgcgaaatt actcgcttct tcgtggatcg cggtttcctg     780
gagatcaaat ctccgattct gattccgctg gaatacattg aacgtatggg catcgataat     840
gataccgaac tgtctaaaca gatcttccgt gtggataaaa acttctgtct gcgtccgatg     900
ctgtctccga acctgtacaa ctatatgcgt aaactggacc gtgccctgcc ggacccgatc     960
aaattgttcg agatcggtcc ttgctaccgt aaagagtccg acggtaaaga gcacctgaa    1020 gaattcacca tgctggcttt cggtcagatg ggtagcggtt gcacgcgtga aaacctggaa    1080
tccattatca ccgacttcct gaatcacctg ggtatcgatt tcaaaattgt tggtgacagc    1140
tgtatggtgt atggcgatac gctggatgtt atgcacggcg atctggagct gtcttccgca    1200
gttgtgggcc aatcccgct ggatcgtgag tggggtatcg acaaacctac gatcggtgcg    1260
ggttttggtc tggagcgtct gctgaaagta aaacacgact tcaagaacat caaacgtgct    1320
```
gcacgttccg agtcctatta caatggtatt tctactaacc tgtaa                1365

<210> SEQ ID NO 2
<211> LENGTH: 454
<212> TYPE: PRT
<213> ORGANISM: Methanosarcina mazei
<220> FEATURE:
<223> OTHER INFORMATION: mutant pyrrolysyl-tRNA synthetase

<400> SEQUENCE: 2

```
Met Asp Lys Lys Pro Leu Asn Thr Leu Ile Ser Ala Thr Gly Leu Trp
1               5                   10                  15

Met Ser Arg Thr Gly Thr Ile His Lys Ile Lys His His Glu Val Ser
                20                  25                  30

Arg Ser Lys Ile Tyr Ile Glu Met Ala Cys Gly Asp His Leu Val Val
            35                  40                  45

Asn Asn Ser Arg Ser Ser Arg Thr Ala Arg Ala Leu Arg His His Lys
        50                  55                  60

Tyr Arg Lys Thr Cys Lys Arg Cys Arg Val Ser Asp Glu Asp Leu Asn
65                  70                  75                  80

Lys Phe Leu Thr Lys Ala Asn Glu Asp Gln Thr Ser Val Lys Val Lys
                85                  90                  95

Val Val Ser Ala Pro Thr Arg Thr Lys Lys Ala Met Pro Lys Ser Val
            100                 105                 110

Ala Arg Ala Pro Lys Pro Leu Glu Asn Thr Glu Ala Ala Gln Ala Gln
        115                 120                 125

Pro Ser Gly Ser Lys Phe Ser Pro Ala Ile Pro Val Ser Thr Gln Glu
    130                 135                 140

Ser Val Ser Val Pro Ala Ser Val Ser Thr Ser Ile Ser Ser Ile Ser
145                 150                 155                 160

Thr Gly Ala Thr Ala Ser Ala Leu Val Lys Gly Asn Thr Asn Pro Ile
                165                 170                 175

Thr Ser Met Ser Ala Pro Val Gln Ala Ser Ala Pro Ala Leu Thr Lys
            180                 185                 190

Ser Gln Thr Asp Arg Leu Glu Val Leu Leu Asn Pro Lys Asp Glu Ile
        195                 200                 205

Ser Leu Asn Ser Gly Lys Pro Phe Arg Glu Leu Glu Ser Glu Leu Leu
    210                 215                 220

Ser Arg Arg Lys Lys Asp Leu Gln Gln Ile Tyr Ala Glu Glu Arg Glu
225                 230                 235                 240

Asn Tyr Leu Gly Lys Leu Glu Arg Glu Ile Thr Arg Phe Phe Val Asp
                245                 250                 255

Arg Gly Phe Leu Glu Ile Lys Ser Pro Ile Leu Ile Pro Leu Glu Tyr
            260                 265                 270

Ile Glu Arg Met Gly Ile Asp Asn Asp Thr Glu Leu Ser Lys Gln Ile
        275                 280                 285

Phe Arg Val Asp Lys Asn Phe Cys Leu Arg Pro Met Leu Ser Pro Asn
    290                 295                 300

Leu Tyr Asn Tyr Met Arg Lys Leu Asp Arg Ala Leu Pro Asp Pro Ile
305                 310                 315                 320

Lys Leu Phe Glu Ile Gly Pro Cys Tyr Arg Lys Glu Ser Asp Gly Lys
                325                 330                 335

Glu His Leu Glu Glu Phe Thr Met Leu Ala Phe Gly Gln Met Gly Ser
            340                 345                 350

Gly Cys Thr Arg Glu Asn Leu Glu Ser Ile Ile Thr Asp Phe Leu Asn
```

```
            355                 360                 365
His Leu Gly Ile Asp Phe Lys Ile Val Gly Asp Ser Cys Met Val Tyr
    370                 375                 380

Gly Asp Thr Leu Asp Val Met His Gly Asp Leu Glu Leu Ser Ser Ala
385                 390                 395                 400

Val Val Gly Pro Ile Pro Leu Asp Arg Glu Trp Gly Ile Asp Lys Pro
                405                 410                 415

Thr Ile Gly Ala Gly Phe Gly Leu Glu Arg Leu Leu Lys Val Lys His
            420                 425                 430

Asp Phe Lys Asn Ile Lys Arg Ala Ala Arg Ser Glu Ser Tyr Tyr Asn
        435                 440                 445

Gly Ile Ser Thr Asn Leu
    450

<210> SEQ ID NO 3
<211> LENGTH: 419
<212> TYPE: PRT
<213> ORGANISM: Methanosarcina barkeri
<220> FEATURE:
<223> OTHER INFORMATION: mutant pyrrolysyl-tRNA synthetase

<400> SEQUENCE: 3

Met Asp Lys Lys Pro Leu Asp Val Leu Ile Ser Ala Thr Gly Leu Trp
1               5                   10                  15

Met Ser Arg Thr Gly Thr Leu His Lys Ile Lys His His Glu Val Ser
            20                  25                  30

Arg Ser Lys Ile Tyr Ile Glu Met Ala Cys Gly Asp His Leu Val Val
        35                  40                  45

Asn Asn Ser Arg Ser Cys Arg Thr Ala Arg Ala Phe Arg His His Lys
    50                  55                  60

Tyr Arg Lys Thr Cys Lys Arg Cys Arg Val Ser Asp Glu Asp Ile Asn
65                  70                  75                  80

Asn Phe Leu Thr Arg Ser Thr Glu Ser Lys Asn Ser Val Lys Val Arg
            85                  90                  95

Val Val Ser Ala Pro Lys Val Lys Lys Ala Met Pro Lys Ser Val Ser
            100                 105                 110

Arg Ala Pro Lys Pro Leu Glu Asn Ser Val Ser Ala Lys Ala Ser Thr
        115                 120                 125

Asn Thr Ser Arg Ser Val Pro Ser Pro Ala Lys Ser Thr Pro Asn Ser
    130                 135                 140

Ser Val Pro Ala Ser Ala Pro Ala Pro Ser Leu Thr Arg Ser Gln Leu
145                 150                 155                 160

Asp Arg Val Glu Ala Leu Leu Ser Pro Glu Asp Lys Ile Ser Leu Asn
                165                 170                 175

Met Ala Lys Pro Phe Arg Glu Leu Glu Pro Glu Leu Val Thr Arg Arg
            180                 185                 190

Lys Asn Asp Phe Gln Arg Leu Tyr Thr Asn Asp Arg Glu Asp Tyr Leu
        195                 200                 205

Gly Lys Leu Glu Arg Asp Ile Thr Lys Phe Phe Val Asp Arg Gly Phe
    210                 215                 220
```

```
Leu Glu Ile Lys Ser Pro Ile Leu Ile Pro Ala Glu Tyr Val Glu Arg
225                 230                 235                 240

Met Gly Ile Asn Asn Asp Thr Glu Leu Ser Lys Gln Ile Phe Arg Val
                245                 250                 255

Asp Lys Asn Leu Cys Leu Arg Pro Met Leu Ser Pro Thr Leu Tyr Asn
            260                 265                 270

Tyr Met Arg Lys Leu Asp Arg Ile Leu Pro Gly Pro Ile Lys Leu Phe
        275                 280                 285

Glu Val Gly Pro Cys Tyr Arg Lys Glu Ser Asp Gly Lys Glu His Leu
    290                 295                 300

Glu Glu Phe Thr Met Val Ala Phe Gly Gln Met Gly Ser Gly Cys Thr
305             310                 315                 320

Arg Glu Asn Leu Glu Ala Leu Ile Lys Glu Phe Leu Asp Tyr Leu Glu
                325                 330                 335

Ile Asp Phe Glu Ile Val Gly Asp Ser Cys Met Val Tyr Gly Asp Thr
            340                 345                 350

Leu Asp Ile Met His Gly Asp Leu Glu Leu Ser Ser Ala Val Val Gly
        355                 360                 365

Pro Val Ser Leu Asp Arg Glu Trp Gly Ile Asp Lys Pro Thr Ile Gly
    370                 375                 380

Ala Gly Phe Gly Leu Glu Arg Leu Leu Lys Val Met His Gly Phe Lys
385             390                 395                 400

Asn Ile Lys Arg Ala Ser Arg Ser Glu Ser Tyr Tyr Asn Gly Ile Ser
                405                 410                 415

Thr Asn Leu
```

SITE-SPECIFIC GENERATION OF PHOSPHORYLATED TYROSINES IN PROTEINS

CROSS-REFERENCE TO RELATED APPLICATIONS

This application claims priority to International Application No. PCT/US2018/018063, entitled "SITE-SPECIFIC GENERATION OF PHOSPHORYLATED TYROSINES IN PROTEINS," filed on Feb. 13, 2018, which claims priority to U.S. Provisional Application No. 62/458,557, entitled "SITE-SPECIFIC GENERATION OF PHOSPHORYLATED TYROSINES IN PROTEINS," filed on Feb. 13, 2017, each of which is incorporated by reference herein in its entirety.

STATEMENT REGARDING FEDERALLY SPONSORED RESEARCH OR DEVELOPMENT

This invention was made with government support under grant no. RO1 GM118384, awarded by the National Institutes of Health. The government has certain rights in the invention.

REFERENCE TO SEQUENCE LISTING, A TABLE, OR A COMPUTER PROGRAM LISTING COMPACT DISK APPENDIX

The instant application contains a Sequence Listing which has been filed electronically in ASCII format and is hereby incorporated by reference in its entirety. Said ASCII copy, created on Feb. 13, 2018, is named UCSF039PCT_SL.txt and is 9,893 bytes in size.

BACKGROUND OF THE INVENTION

Protein phosphorylation is a major post-translational modification that plays a pivotal role for signal transduction and in regulating cellular events. In particular, phosphorylation of tyrosine is involved in many processes including cell proliferation, cell cycle progression, metabolic homeostasis, transcriptional activation, neural transmission, differentiation and development, and aging. Conversely, dysfunction of tyrosine phosphorylation results in various diseases, most prominently in cancer. The limited access to site-specifically phosphorylated proteins hampers the investigation of this major post-translational modification in disease-relevant proteins. Many methods have been developed to prepare and study tyrosine phosphorylated proteins. The most generally useful approach has been the substitution of negatively charged glutamate or aspartate in place of phosphoserine or phosphothreonine modifications, despite the charge difference between the carboxylate and phosphate mono-ester. Mimics of the aromatic phosphotyrosine however are particularly challenging since there are no aromatic negatively charged residues in the natural 20 amino acids. Proteins can be phosphorylated by employing tyrosine kinases, but in vitro kinase phosphorylation has limited site specificity, and often results in less than stoichiometric phosphorylation.

To overcome this limitation, chemical approaches including native chemical ligation, semisynthetic and cell-free methods have been developed to introduce phosphotyrosine site-selectively, yet these methods are technically challenging and cannot be generally applied to all proteins. Through the expansion of the genetic code, chemical analogues of phosphotyrosine were selectively incorporated into proteins in $E.$ $coli$, yet these analogues cannot faithfully mimic the phosphate group and its negative charges. Another phosphorylated amino acid, phosphoserine, has recently been genetically incorporated into proteins in $E.$ $coli$, although the expressed protein has low yields and low quality due to codon skipping. In spite of extensive efforts to satisfy the high demand for pure phosphorylated proteins for investigating phosphorylation, to date, there is no general, efficient system available to prepare proteins with native phosphotyrosine introduced site-specifically.

Accordingly, there remains a need in the art for efficient and simple methods of producing proteins with site-specific phosphorylated tyrosines.

SUMMARY OF THE INVENTION

Provided herein are novel materials and methods for site-specific incorporation of phosphotyrosines into proteins. The methods of the invention encompass the use of a novel aminoacyl tRNA synthetase capable of charging certain tRNAs with a phosphotyrosine precursor. The phosphotyrosine precursor is then incorporated, site-specifically, into a protein at sites where phosphotyrosine residues are desired. The phosphotyrosine precursors are subsequently treated to convert them into phosphotyrosine residues, yielding proteins with phosphotyrosines at selected sites. The scope of the invention encompasses novel aminoacyl tRNA synthetases, novel phosphotyrosine precursors, and methods of using these materials to create site-specific phosphorylated tyrosine residues in a protein.

DETAILED DESCRIPTION OF THE INVENTION

Figure 1:
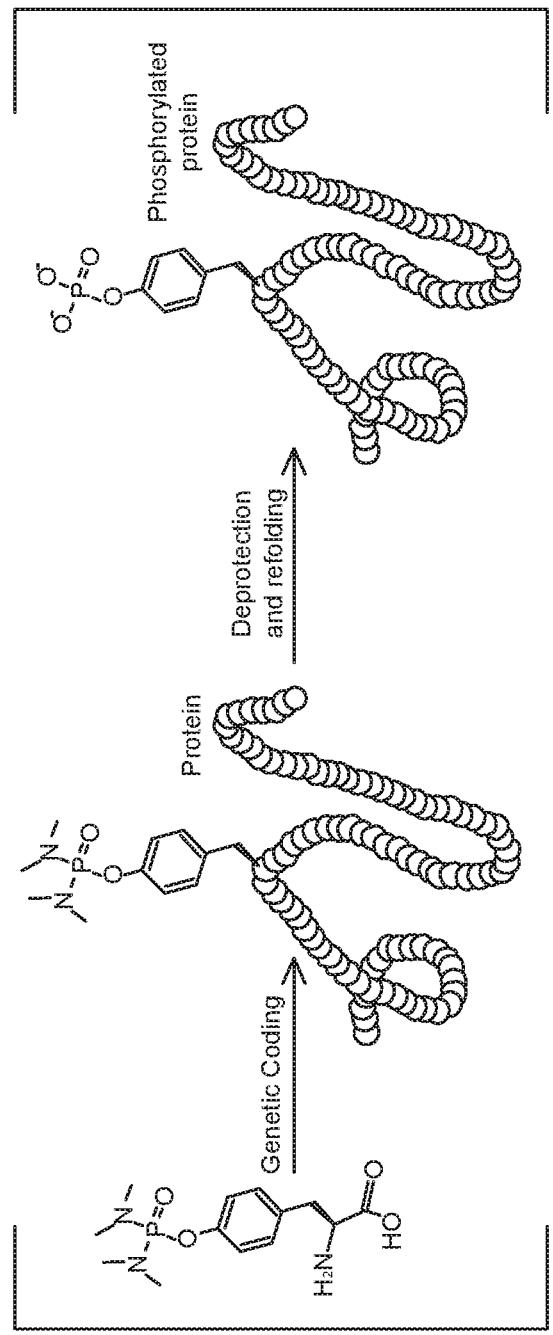
FIG. 1 is a schematic presentation of the production of pure tyrosine phosphorylated proteins. Genetic encoding of a phosphotyrosine precursor ($Tyr(PO(NMe_2)_2$) into proteins and subsequent deprotection results in formation of a native phosphotyrosine, site-specifically.
Figure 2:
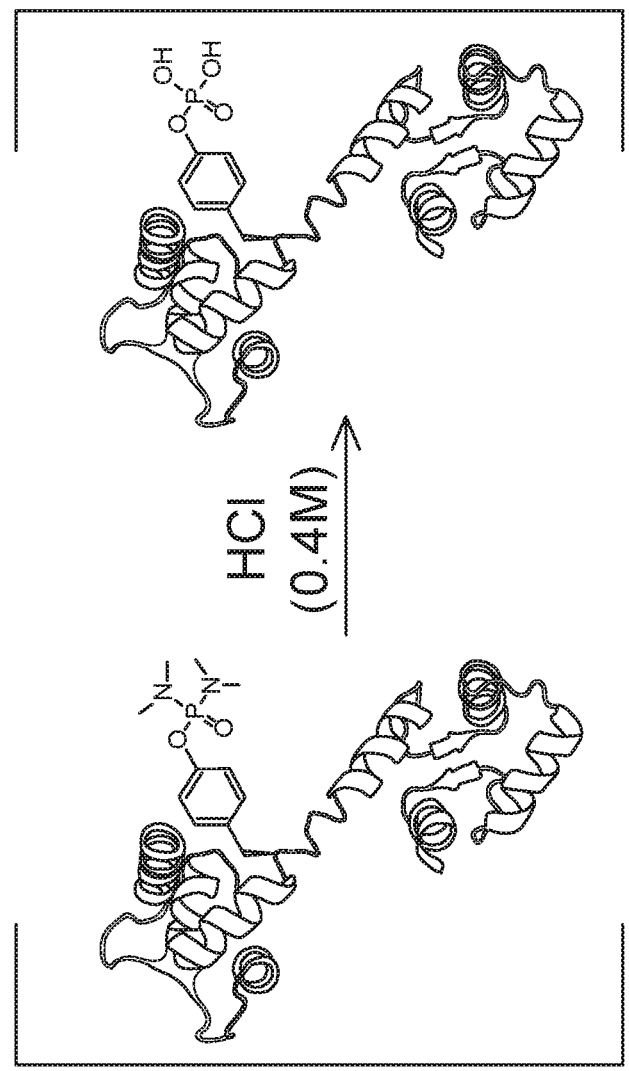
FIG. 2 depicts genetic encoding of the the phosphotyrosine precursor $Tyr(PO(NMe_2)_2$ into calmodulin, acidic cleavage of the protecting group and formation of phosphorylated calmodulin by mild acidic treatment.
Figure 3:
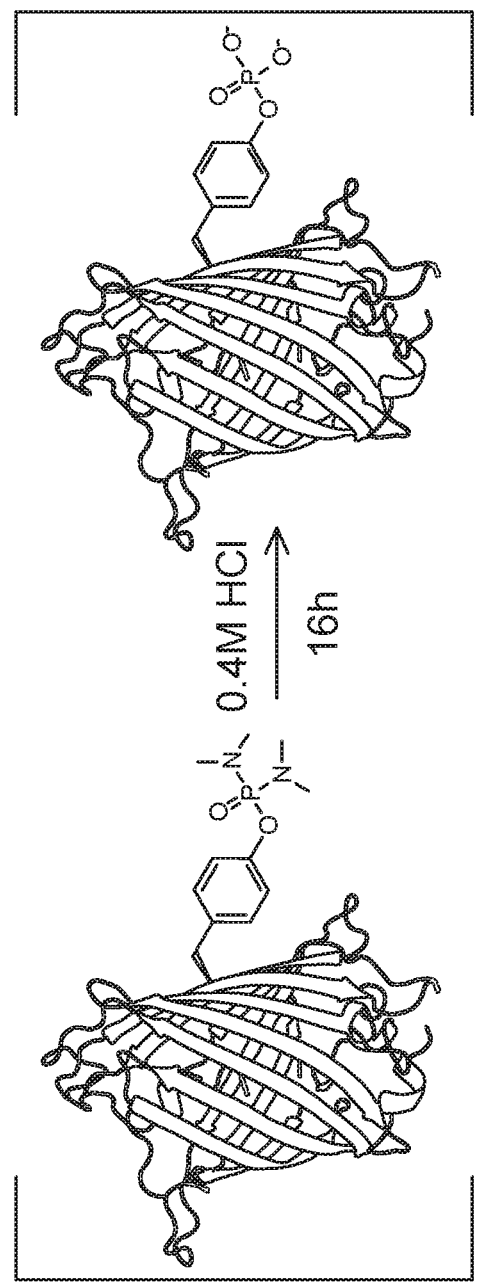
FIG. 3 depicts genetic encoding of $Tyr(PO(NMe_2)_2$ into GFP, acidic cleavage of the protecting group, and formation of phosphorylated GFP.
Figure 4:
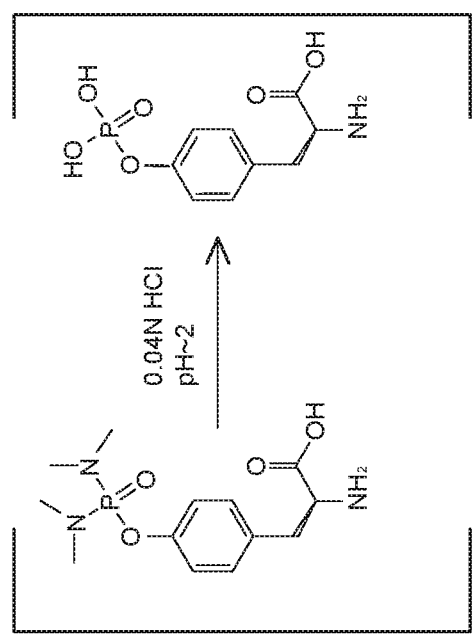
FIG. 4 depicts HCl cleavage of the phosphoramidate group in $Tyr(PO(NMe_2)_2$ and formation of phosphorylated tyrosine.

The inventions disclosed herein provide the art with novel materials and methods for the facile, site-specific incorporation of phosphorylated tyrosines into proteins. In a general aspect, the scope of the invention encompasses a method of creating proteins with selectively phosphorylated tyrosine residues as follows: a charge-neutral and stable phosphotyrosine analogue is genetically incorporated into proteins at the target phosphorylation site through the expansion of the genetic code, which precursors are subsequently converted into native phosphorylated tyrosines by a mild treatment, such as a facile pH shift.

The general method of the invention utilizes the following elements:
- a "phosphorylated tyrosine precursor" that comprises an amino acid that can be converted to a phosphorylated tyrosine upon application of a conversion treatment;
- incorporation of the phosphorylated tyrosine precursor into selected sites of a "precursor protein" by use of an expression system;
- a "mutant aminoacyl tRNA synthetase" and compatible tRNA, wherein these two elements are capable of incorporating a phosphorylated tyrosine precursor into a protein at sites specified by a non-natural codon; and
- a "conversion treatment" comprising a mild chemical or energetic treatment that converts the phosphorylated tyrosine precursor to a phosphorylated tyrosine.

The general method of the invention encompasses the steps of:
- producing a nucleic acid construct that codes for the precursor protein, wherein the nucleic acid construct comprises a non-natural codon at each position wherein a phosphorylated tyrosine precursor is to be included in the precursor protein;
- introducing the engineered nucleic acid sequence into an expression system wherein the expression system comprises the mutant aminoacyl tRNA synthetase and compatible tRNA, as well as phosphorylated tyrosine precursors;
- inducing the expression system to express the precursor protein, wherein one or more phosphorylated tyrosine precursors are incorporated into the protein at positions specified by the non-natural codon(s);
- isolating the expressed precursor protein; and
- treating the precursor protein with the conversion treatment to convert the one or more phosphorylated tyrosine precursors to phosphorylated tyrosines.

The scope of the invention encompasses various implementations of the aforementioned method, the various elements of which are next described in detail.

Phosphorylated Protein.

The objective of the invention is to provide proteins having one or more phosphorylated tyrosine residues. The phosphorylated protein may comprise any protein known in the art, or a fragment thereof, or may encompass artificial polypeptide sequences. Exemplary phosphorylated proteins include growth factors, growth factor receptors, enzymes, transcription factors, and biologically active proteins, e.g., those wherein phosphorylation of tyrosines is implicated in their activity. The basic operation of the invention is to produce a protein with one or more phosphorylated tyrosine residues, at a selected position or positions. In one implementation, the selected protein is a native protein found in vivo that is the target of phosphorylation. The phosphorylation sites may comprise tyrosine residues that are known to be or which are putatively phosphorylated by regulatory kinases in vivo. Alternatively, the phosphorylated tyrosine(s) may be placed at one or more novel positions, for example, comprising tyrosine residues that are not normally phosphorylated or substituting phosphorylated tyrosines for other residues.

Precursor Protein Nucleic Acid Template.

The phosphorylated proteins of the invention are formed with the use of a nucleic acid construct coding therefore, wherein the amino acid residues specifying phosphorylated tyrosines are coded by non-natural codons. For example, such sites may comprise the amber codon (TAG), ochre codon (TAA), or umber codon (TGA).

The phosphorylated protein template may be in any nucleic acid form, typically DNA. The phosphorylated protein template may be present in any construct, for example, in a form compatible with use in an expression system. For example, the phosphorylated protein template may comprise a circularized plasmid, a linearized plasmid, or may be stably integrated into the genome of an organism. The construct may comprise any elements required for expression, including promoters, repressor elements, enhancer elements, etc.

The nucleic acid sequence may further code for motifs or elements that will facilitate the isolation and purification of the target protein produced therefrom. For example, in one embodiment, the target protein nucleic acid sequence codes for a terminal HIS tag, for example a 6×HIS tag.

Phosphorylated Tyrosine Precursor.

One element of the invention is the use of a non-natural amino acid comprising a phosphorylated tyrosine precursor. The non-natural amino acid will comprise an amino acid with structure:

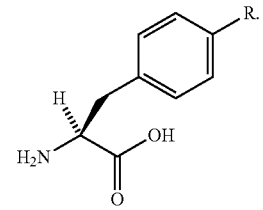

The amino acid will have the following properties: A first property of the amino acid is that R will be neutral, having no charge, or a small charge, e.g. a net negative charge of −1 or less. Phosphorylated tyrosine has two negative charges and its diffusion across the cell membrane is not energetically favorable, making it hard to attain sufficient intracellular concentrations for protein translation therewith. Accordingly, the phosphorylated tyrosine precursors of the invention comprises a neutral species which efficiently diffuses into cells, for example cells used in an expression system as described below.

A second property is that the amino acid will be resistant to phosphatases, which are ubiquitous within the cell. Phosphorylated tyrosine itself is vulnerable to phosphatase activity and does not persist in the cellular environment. The phosphorylated tryosine precursor amino acids of the invention, in contrast, will comprise species that are not acted upon by phosphatases.

A third property of the phosphorylated tryosine precursor amino acid is that it is elongation competent. Phosphorylated tyrosine itself does not efficiently incorporate into proteins by the cellular translation machinery due to the presence of the negatively charged functional group. In contrast, the phosphorylated tryosine precursor amino acids of the invention comprise species which are compatible with the translation machinery of organisms such as *E. coli* and other expression vectors.

A fourth property of the amino acid is that it can be converted into a phosphorylated tyrosine by a chemical or energetic treatment under mild conditions. "Mild conditions," as used herein, means conditions which do not substantially alter the protein's composition or disrupt proper folding of the protein. For example, in one embodiment, the treatment is a mild acid treatment, as described below.

The R group may comprise any species which can be converted to a phosphoric acid group under selected conditions. In one embodiment, the R group comprises a species that can be modified in a chemical reaction with one or more reactants under mild conditions to produce a phosphoric acid group. In one embodiment, the R group comprises a phosphoramidate group. For example, the phosphorylated tyrosine precursor may comprise the amino acid (S)-3-(4(bis (dimethylamino)phosphoryloxy) phenyl)propanoic acid (Tyr(PO(NMe$_2$)$_2$):

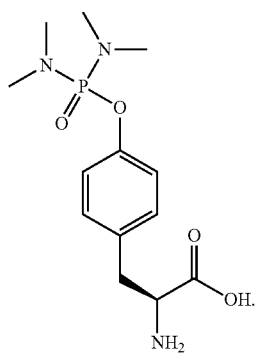 [SMILES: CN(C)P(=O)(Oc1ccc(C[C@H](N)C(=O)O)cc1)N(C)C]

In another implementation, the R group comprises a protecting group that is subsequently cleaved or degraded to reveal or produce a phosphoric acid group, for example by exposure to light. In one embodiment, the phosphorylated tyrosine precursor comprises light-cleavable o-nitrobenzyl groups. For example, in one embodiment, the phosphorylated tyrosine precursor comprises the amino acid (S)-4-(2-amino-2-carboxyethyl)phenyl 2-nitrobenzyl phosphate:

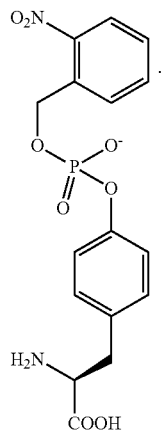

In another embodiment, the amino acid comprises (S)-4-(2-amino-2-carboxyethyl)phenyl 4,5-dimethoxy-2-nitrobenzyl phosphate:

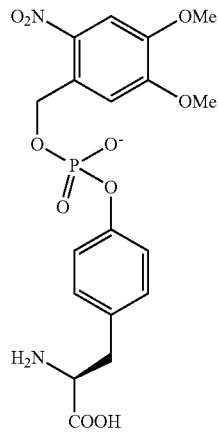 [SMILES: COc1cc(COP(=O)([O-])Oc2ccc(C[C@H](N)C(=O)O)cc2)c([N+](=O)[O-])cc1OC]

In another embodiment, the R group comprises a species that can be substituted with a phosphoric acid group under mild conditions.

Mutant Aminoacyl tRNA Synthetase.

The invention encompasses the use of an engineered expression system that can site-specifically incorporate a phosphorylated tyrosine precursor into a protein. The expression system will comprise (a) a tRNA which can be charged with the phosphorylated tyrosine precursor and which will recognize a non-natural codon; and (b) an engineered aminoacyl tRNA synthetase which is capable of charging the tRNA with the phosphorylated tyrosine precursor.

In one embodiment, the aminoacyl tRNA synthetase is a mutant form of the *Methanosarcina mazei* pyrrolysyl-tRNA synthetase, as known in the art, for example, as specified by Uniprot Accession Numbers Q8PWY1, A0A0E3WPC9 A0A0E3RZQ6, A0A0E3PZI8, A0A0E3LT83, A0A0E3RUJ0, A0A0F8GPG2, A0A0F8JXW8, or A0A0F8HMA4.

In one embodiment, the mutant is a *Methanosarcina mazei* pyrrolysyl-tRNA synthetase (or variant thereof) comprising one or more amino acid substitutions selected from the group consisting of: Ser302, Met309, Leu322, Ala346, Gly348, Val401, Thr417, and Gly419. In one embodiment, the *Methanosarcina mazei* pyrrolysyl-tRNA synthetase comprises a polypeptide of SEQ ID NO: 2, or a variant thereof. Variants of a selected amino acid sequence, as used herein, include truncations, deletions, insertions, and substitutions of the selected sequence. Variants will further include proteins that are at least 80%, at least 85%, at least 90%, or at least 95% identical to the enumerated sequence. In one embodiment, the invention comprises SEQ ID NO: 2 or a variant thereof which has the ability to charge a tRNA with a phosphorylated tyrosine precursor amino acid, for example, (S)-4-(2-amino-2-carboxyethyl)phenyl 2-nitrobenzyl phosphate.

In another embodiment, the aminoacyl tRNA synthetase can be a mutant form of the *Methanosarcina barkeri* pyrrolysyl-tRNA synthetase, as known in the art, for example, as specified by Uniprot Accession Numbers Q46E77, Q6WRH6, A0A0G3CC06, or A0A0E3QQZ0. In one embodiment, the mutant is a *Methanosarcina barkeri* pyrrolysyl-tRNA synthetase (or variant thereof) comprising one or more amino acid substitutions selected from the group consisting of: Ser267, Met274, Leu287, Ala311, Gly313, Val366, Thr382, and Gly384. In one embodiment, the invention comprises SEQ ID NO: 3 or a variant thereof which has the ability to charge a tRNA with a phosphorylated tyrosine precursor amino acid, for example, (S)-4-(2-amino-2-carboxyethyl)phenyl 2-nitrobenzyl phosphate.

The mutant aminoacyl tRNA synthetase will be utilized in the expression system with a compatible tRNA, which such tRNA is capable of being charged with a phosphotyrosine precursor and which is competent for the incorporation of the phosphotyrosine precursor into a protein during translation.

In one embodiment, the tRNA is the *Methanosarcina mazei* pyrrolysyl-tRNA, as known in the art. In another embodiment, the tRNA is the *Methanosarcina barkeri* pyrrolysyl-tRNA, as known in the art. These tRNAs will incorporate their amino acids at the amber stop codon, TAG. Other tRNAs that may be used include the tRNA$^{M15}$ and other tRNAs described in Serfling et al., 2018 "Designer tRNAs for efficient incorporation of non-canonical amino acids by the pyrrolysine system in mammalian cells", Nuc. Acids Res. 46(1):1-10.

Engineered Expression Systems.

The scope of the invention encompasses an engineered protein expression system comprising a tRNA-aminoacyl tRNA synthetase pair, as described above. The expression system may comprise any expression system, including, for example, bacterial, yeast, plant, and mammalian expression systems known in the art. The expression system may comprise a cell-free protein synthesis system, for example a cell lysate-based cell free protein synthesis system.

The engineered protein expression system may comprise cells (or the lysates of such cells), wherein the cells are engineered to express a mutant aminoacyl tRNA synthetase and tRNA pair capable of incorporating phosphorylated tyrosine precursors into a protein.

For example, in one embodiment, the expression vector comprises an *E. coli* expression vector. In other embodiments, the expression vector may comprise a yeast, plant, or mammalian expression system. For example, the expression systems may comprise *Escherichia coli* S30, rabbit reticulocyte, or wheat germ expression systems.

In one embodiment, the engineered expression system comprises a cell expressing a mutant *Methanosarcina mazei* pyrrolysyl-tRNA synthetase and a compatible tRNA. In one embodiment, the expression system comprises a cell comprising a nucleic acid sequence that codes for a mutant *Methanosarcina mazei* pyrrolysyl-tRNA synthetase comprising one or more amino acid substitutions selected from the group consisting of Ser302, Met309, Leu322, Ala346, Gly348, Val401, Thr417, and Gly419.

In one embodiment, the cell comprises a cell which expresses the protein of SEQ ID NO: 2 or a variant thereof. In one embodiment, the expression system comprises a cell comprising the nucleic acid sequence of SEQ ID NO: 1 or a variant thereof. In one embodiment, the scope of the invention comprises a nucleic acid construct comprising SEQ ID NO: 1 or a variant thereof. Variants of SEQ ID NO: 1 include truncations, deletions, insertions, and nucleic acid substitutions of the recited sequence. Variants will further include nucleic acid sequences that are at least 80%, at least 85%, at least 90%, or at least 95% identical to SEQ ID NO: 1 and which code for a pyrrolysyl-tRNA synthetase having the ability to charge a tRNA with a phosphorylated tyrosine precursor amino acid, for example, (S)-4-(2-amino-2-carboxyethyl)phenyl 2-nitrobenzyl phosphate.

In an alternative embodiment, the cell comprises nucleic acid sequences coding for a *Methanosarcina barkeri* aminoacyl pyrrolysyl-tRNA synthetase capable of charging a tRNA with a phosphotyrosine precursor. In one embodiment, the cell comprises a nucleic acid sequence coding for the protein of SEQ ID NO: 3 or a variant thereof. In one embodiment, the cell comprises a cell which expresses the protein of SEQ ID NO: 3 or a variant thereof.

In the expression systems of the invention, the tRNA and aminoacyl tRNA synthetase elements may be constitutively expressed, transiently expressed, or inducibly expressed, as desired.

Precursor Protein Synthesis.

The expression system is induced to produce a precursor protein, the precursor protein comprising a protein or polypeptide wherein one or more amino acid residues comprises a phosphorylated tyrosine precursor. The expression system is induced by supplying to it constituents and any conditions necessary for production of the precursor protein. The constituents necessary for production of the precursor protein will include: amino acids, including amino acids comprising one or more phosphorylated tyrosine precursors compatible with the tRNA:tRNA synthetase of the expression system; the engineered nucleic acid construct coding for the precursor protein; and any other components necessary for the expression system to produce the precursor protein. The precursor protein will then be produced, incorporating the phosphorylated tyrosine precursor site-specifically at the one or more sites specified by the non-natural codons.

Following protein expression, the precursor protein may be isolated from the protein expression system by relevant methods known in the art. For example, in the case of a cellular expression system, protein isolation may be facilitated by cell lysis. Protein may be isolated by chromatography, electrophoresis, affinity purification techniques, HPLC, or any other techniques known in the art. In one embodiment, the precursor protein comprises a HIS tag and is purified by use of a nickel affinity column or like platforms.

Converting Precursor Protein to Proteins Comprising Site-Specific Phosphorylated Tyrosines.

The isolated precursor protein may then be treated utilizing appropriate methods to convert the phosphorylated tyrosine precursors incorporated therein to phosphorylated tyrosine residues.

In one implementation, the phosphorylated tyrosine precursor comprises a phosphorylated tyrosine precursor which converts to a phosphorylated tyrosine under acidic conditions. For example, the treatment may comprise exposure of the precursor protein to a solution having pH between 1-4, for example, exposure for 6-48 hours, at temperatures from 2-25° C., for example, 4° C. or room temperature. For example, exposure to a solution of 0.04 M HCl for 36 hours at room temperature could be utilized. For example, acidic treatment may be used to convert phosphorylated tyrosine precursors comprising a phosphoramidate group, for example, the phosphorylated tyrosine precursor (S)-3-(4(bis (dimethylamino)phosphoryloxy) phenyl)propanoic acid $(Tyr(PO(NMe_2)_2))$.

In one implementation, the phosphorylated tyrosine precursor comprises a protecting group which converts to a phosphorylated tyrosine under conditions which remove the protecting group. For example, if the protecting group is a light-activated protecting group, the treatment will comprise exposure to the appropriate wavelengths of light to degrade or remove the protecting group. For example, if the phosphorylated tyrosine precursor comprises light-cleavable o-nitrobenzyl groups, exposure to wavelengths of 200-320 nm will result in cleavage of the protecting moiety and formation of a phosphorylated tyrosine.

In one embodiment, the protein extraction and phosphotyrosine conversion steps are merged into a single step, for example, an acid lysis which liberates expressed proteins from the cells comprising the expression system and which also converts the phosphorylated tyrosine precursors to phosphorylated tyrosine residues.

Phosphorylated Proteins.

The scope of the invention further encompasses proteins comprising one or more phosphorylated tyrosine residues wherein such proteins were produced using any of the methods or compositions of the invention described herein. The scope of the invention extends to the use of phosphorylated proteins made by the method of the invention in research and clinical contexts.

EXAMPLES

Example 1. Synthesis of a Phosphorylated Tyrosine Precursor Amino Acid

The phosphorylated tyrosine precursor amino acid (Tyr(PO(NMe$_2$)$_2$):

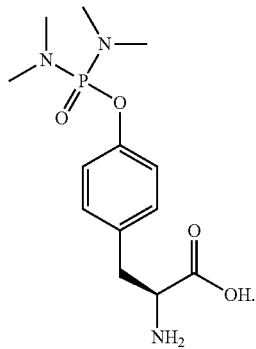 [SMILES: CN(C)P(=O)(Oc1ccc(C[C@H](N)C(=O)O)cc1)N(C)C]

was synthesized as follows: (S)-2-(((9H-fluoren-9-yl)methoxy)carbonylamino)-3-(4(bis(dimethylamino)phosphoryloxy) phenyl)propanoic acid (250 mg, 0.46 mmol) was dissolved in 3 mL 20%-4-methylpiperidine-DMF and stirred at room temperature for 20 min. Subsequently, the reaction mixture was added to cold Et$_2$O. The formed precipitate was removed and dried in vacuo to yield 120 mg (82%) of the final pure product.

Example 2. Evolution of a Mutant Aminoacyl tRNA Synthetase for the Incorporation of Phosphorylated Tyrosine Precursor Amino Acids into Proteins To genetically encode the phosphorylated tyrosine precursor Tyr(PO(NMe$_2$)$_2$ into proteins, the *Methanosarcina mazei* tRNA$_{CUA}^{Pyl}$/PylRS pair was evolved to be specific for this unnatural amino acid. A mutant library of PylRS was generated with multiple residues: 302, 309, 322, 346, 348, 401, 417, and 419 being mutated as previously described in Hoppmann, C., Lacey, V. K., Louie, G. V., Wei, J., Noel, J. P. & Wang, L. Genetically Encoding Photoswitchable Click Amino Acids in *Escherichia coli* and Mammalian Cells. *Angew. Chem. Int. Ed. Engl.* 53, 3932-3936 (2014). From this library, one round of positive selection identified a clone showing phenotypic dependence on Tyr(PO(NMe$_2$)$_2$. DNA sequencing revealed that this clone carried a mutant PylRS with amino-acid identities Ser302, Gly309, Pro322, Ala346, Gly348, Gly384, Ala401, Gly417, and Ala419, as in SEQ ID NO: 2, which was named as MmNpYRS.

To investigate the efficiency and fidelity of the evolved MmNpYRS to incorporate Tyr(PO(NMe$_2$)$_2$, a gene for *Xenopus* calmodulin (CaM_76 TAGHis6) that contained an amber stop codon TAG at the permissive Met76 site (and a C-terminal His×6 tag) was expressed in *E. coli* BL21 cells, together with the tRNA$_{CUA}^{Pyl}$/MmNpYRS. Analysis of the expressed CaM protein by electrospray ionization ion trap mass spectrometry confirmed incorporation of Tyr(PO(NMe$_2$)$_2$ into CaM at position 76. In addition, the high fidelity of the evolved MmNpYRS was also confirmed by incorporating Tyr(PO(NMe$_2$)$_2$ into another protein, myoglobin. The incorporation of Tyr(PO(NMe$_2$)$_2$ into proteins in *E. coli* suggests that the WT *E. coli* EF-Tu is compatible with Tyr(PO(NMe$_2$)$_2$-tRNA$_{CUA}^{Pyl}$.

Example 3. Conversion of Precursor Protein to Protein Comprising Phosphorylated Tyrosine Residues To test the cleavage of Tyr(PO(NMe$_2$)$_2$ and the formation of the pTyr within proteins, we treated the CaM solution (0.6 mg mL$^{-1}$) with HCl at a final concentration of 0.4 M (pH~1) for 48 h at 4° C. The protein sample was lyophilized to remove the acid and then dissolved in water. ESI-MS measurements clearly demonstrated the removal of the protecting group and the formation of a pTyr within the CaM.

In another experiment, Tyr(PO(NMe$_2$)$_2$ was incorporated in green fluorescent protein (GFP), which has a larger MW (28 kDa) and a different secondary structure β-sheet compared to the largely helical CaM. A mutant GFP gene containing a TAG codon at the permissive Tyr182 site (GFP_182 TAG) and a C-terminal His×6 tag was expressed with the tRNA$_{CUA}^{Pyl}$/MmNpYRS pair in *E. coli* in 2×YT medium. The GFP protein was purified. HCl (final conc. 0.4 M, pH~1) was added to a diluted (0.1 mg mL$^{-1}$) solution of the purified GFP containing, and the mixture was incubated at 4° C. for 16 h, after which the sample was lyophilized and dissolved in water. Western-blot analysis of the GFP proteins using the anti-His×6 antibody showed that full-length GFP was expressed only in the presence of Tyr(PO(NMe$_2$)$_2$, confirming the specific incorporation of Tyr(PO(NMe$_2$)$_2$ by the tRNA$_{CUA}^{Pyl}$/MmNpYRS.

Example 4. Synthesis of Phosphorylated Ubiquitin

The approach described above was used to generate phosphotyrosine ubiquitin and to investigate the impact of tyrosine phosphorylation on the ubiquitin conformation and function. Phosphorylation of Tyr59, the only tyrosine residue of WT ubiquitin, has been exclusively observed in cancerous tissue but its biological relevance remains unknown. The hydroxyl group of Tyr59 hydrogen bonds with the backbone amide of Glu51, forming a loop that is disrupted by mutation of Tyr59 to other natural amino acids. To provide direct evidence whether phosphorylation of tyrosine 59 alters the Y59-E51 loop in ubiquitin and ubiquitin function, Tyr(PO(NMe$_2$)$_2$ was incorporated into ubiquitin at position 59, as above, and the phosphotyrosine was generated by acid cleavage followed by lyophilization. SDS- PAGE in combination with ESI-MS spectroscopic investigations confirmed the successful preparation of pTyr59 ubiquitin.

A conformation change was induced by pTyr59, as confirmed by HSQC NMR spectra of WT ubiquitin and the phosphorylated ubiquitin. To investigate whether the pTyr59 in ubiquitin would interfere with thioester formation between ubiquitin and its E2 conjugating enzyme, the conjugation of the generated phosphorylated ubiquitin to the E2 enzyme UBE2D3 was studied. The phosphorylated ubiquitin showed dramatically decreased formation of the Ub-E2 conjugate, indicating that the phosphorylation of tyrosine 59 disturbs the conformation of ubiquitin and its ability to conjugate to the E2 enzyme UBE2D3, suggesting that Tyr59 phosphorylation on ubiquitin could play negative regulation in the ubiquitination process.

In summary, the results demonstrate a novel method to prepare phosphorylated proteins with phosphotyrosine site-specifically introduced. Combining genetic incorporation with facile pH conversion, this method enables phosphotyrosine to be introduced at different secondary structures of various proteins with broad compatibility of protein type, size, and phosphorylation site. The method produces phosphorylated proteins in high quality and excellent yields.

All patents, patent applications, and publications cited in this specification are herein incorporated by reference to the same extent as if each independent patent application, or publication was specifically and individually indicated to be incorporated by reference. The disclosed embodiments are presented for purposes of illustration and not limitation. While the invention has been described with reference to the described embodiments thereof, it will be appreciated by those of skill in the art that modifications can be made to the structure and elements of the invention without departing from the spirit and scope of the invention as a whole.

What is claimed is:

1. A method of producing a protein comprising phosphorylated tyrosine at a one or more selected positions in the protein, comprising the steps of:

producing a nucleic acid construct that codes for a precursor protein, wherein the precursor protein is the protein comprising phosphorylated tyrosine precursor at the one or more positions selected for introduction of phosphorylated tyrosine; and wherein the nucleic acid construct comprises a one or more non-natural codons comprising a nucleotide sequence of TAG, TGA, or TAA at a one or more positions of the nucleic acid sequence coding for the one or more phosphorylated tyrosine precursors to be included introduced into the precursor protein;

introducing the engineered nucleic acid sequence into an expression system wherein the expression system comprises a mutant aminoacyl tRNA synthetase and a compatible tRNA charged with the phosphorylated tyrosine precursor;

wherein the mutant aminoacyl tRNA synthetase and the compatible tRNA are capable of incorporating the one or more phosphorylated tryosine precursors into the precursor protein at the one or more positions of the engineered nucleic acid sequence comprising the one or more non-natural codons;

wherein the phosphorylated tyrosine precursor comprises

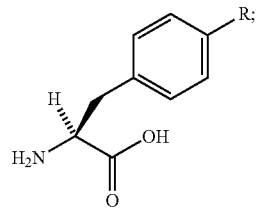

wherein R comprises a phosphoramidate group;

and wherein:

the mutant aminoacyl tRNA synthetase comprises a mutant *Methanosarcina mazei* pyrrolysyl-tRNA synthetase having a sequence with at least 95% identity to SEQ ID NO: 2 and comprises serine at amino acid position 302, methionine at amino acid position 309, leucine at amino acid position 322, alanine at amino acid position 346, glycine at amino acid position 348, and threonine at amino acid position 417 or the mutant aminoacyl tRNA synthetase comprises a mutant *Methanosarcina barkeri* pyrrolysyl-tRNA synthetase having a sequence with at least 95% identity to SEQ ID NO: 3 and comprises serine at amino acid position 267, methionine at amino acid position 274, leucine at amino acid position 287, alanine at amino acid position 311, glycine at amino acid position 313, and threonine at amino acid position 382;

inducing the expression system to express the precursor protein;
isolating the expressed precursor protein; and
treating the precursor protein with a chemical or energetic treatment that converts the one or more phosphorylated tyrosine precursors therein to phosphorylated tyrosines.

2. The method of claim 1, wherein
the phosphorylated tyrosine precursor comprises

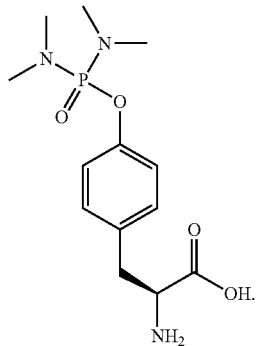 [SMILES: CN(C)P(=O)(Oc1ccc(C[C@H](N)C(=O)O)cc1)N(C)C]

3. The method of claim 1, wherein
the mutant aminoacyl tRNA synthetase comprises a protein having a sequence with at least 95% identity to SEQ ID NO: 2 and comprises serine at amino acid position 302, methionine at amino acid position 309, leucine at amino acid position 322, alanine at amino acid position 346, glycine at amino acid position 348, and threonine at amino acid position 417.

4. The method of claim 1, wherein
the mutant aminoacyl tRNA synthetase comprises a protein having a sequence with at least 95% identity to SEQ ID NO: 3 and comprises serine at amino acid position 267, methionine at amino acid position 274, leucine at amino acid position 287, alanine at amino acid position 311, glycine at amino acid position 313, and threonine at amino acid position 382.

5. The method of claim 1, wherein the chemical or energetic treatment comprises exposure of the precursor protein to mild acidic conditions.

* * * * *